United States Patent [19]
Chung et al.

[11] Patent Number: 6,046,230
[45] Date of Patent: Apr. 4, 2000

[54] STABLE INJECTION FORMULATION CONTAINING PACLITAXEL

[75] Inventors: Kyu-Nung Chung, Samick Apt 2-205, #1681 SeoCho-Dong, SeoChu-Ku; Yhun-Yhong Sheen; Hyun-Jong Shin, all of Seoul, Rep. of Korea

[73] Assignee: Kyu-Nung Chung, Seoul, Rep. of Korea

[21] Appl. No.: 09/400,343

[22] Filed: Sep. 20, 1999

[30] Foreign Application Priority Data

Mar. 23, 1998 [KR] Rep. of Korea ......................... 99-9928

[51] Int. Cl.[7] .................................................. A61K 31/335
[52] U.S. Cl. .............................................................. 514/449
[58] Field of Search ............................................. 514/449

[56] References Cited

U.S. PATENT DOCUMENTS

| 5,681,846 | 10/1997 | Trissel | 514/449 |
| 5,770,222 | 6/1998 | Unger et al. | 424/450 |
| 5,877,205 | 3/1999 | Andersson | 514/449 |
| 5,922,754 | 7/1999 | Burchett et al. | 514/449 |
| 5,925,776 | 7/1999 | Nikolayev et al. | 554/219 |

*Primary Examiner*—William R. A. Jarvis
*Assistant Examiner*—Vickie Y. Kim
*Attorney, Agent, or Firm*—Harrison & Egbert

[57] ABSTRACT

This invention relates to a stable injection paclitaxel formulation having polyoxyethylene sorbitol oleic polyester as a main solubilizer, and appears to have less toxicity and greater stability compared to polyethoxylated castor oil-containing formulation which is clinically used all over the world. The formulation includes paclitaxel 30 mg, povidone 80 mg, oxyethylene sorbitol oleate 0.5 to 2.0 ml, (oxyethylene glycol)$_{15-20}$ fatty acid monoester 0.5 to 2.0 ml, polyethylene glycol 1.0 ml, and anhydrous alcohol 2.0 ml. The oxyethylene sorbitol oleate is either (oxyethylene)$_{60}$ sorbitol tetraoleate or (oxyehtylene)$_{45}$ sorbitol trioleate.

4 Claims, No Drawings

STABLE INJECTION FORMULATION CONTAINING PACLITAXEL

This application claims priority under 35 USC § 119 of Korea 99-9928, filed Mar. 23, 1999.

BACKGROUND OF THE INVENTION

1. Field of the Invention

The present invention relates to an stable injection formulation containing paclitaxel.

2. Description of the Prior Art

Paclitaxel is a diterpenoid compound which is widely used as an antineoplastic agent for the treatment of the breast and ovarian cancers. Also, the clinical tests of the paclitaxel for the other kinds of cancers are presently carried out in several countries. However, because of the extraordinary low solubility of the paclitaxel in water and in the pharmaceutically acceptable solvents (see, Flora K. P. et al, NCI Investigational Drugs Chemical Information, NCI, pp218 (1992), the paclitaxel is limited in its formulation.

Cremophor EL, sold by BASF, is typically used as a solubilizer for the paclitaxel and is a condensation product of ethylene oxide and castor oil. This solubilizer is known to cause a reaction, such as a hyperallergic side reaction, when administered to patients. See, Alka-On Yuksel. H., et al, Pharmaceutical Research 11, 206(1994). Moreover, the injection formulation containing such a solubilizer has less dilution stability, when the formulation is diluted with saline or an aqueous dextrose solution. See, Mead Johnson Oncology (1993). The paclitaxel injection formulation exhibits instability over extended periods of time if an adequate pretreatment of the solubilizer is not foreseen. See, U.S. Pat. No. 5,504,102. A specially designed in-filter-infusion system is thus recommended for the administration of the injection formulation. See, Mead Johnson Oncology (1993).

Meanwhile, the commercial formulation presently available contains paclitaxel 30 mg/1 vial(5 ml), Cremophor EL 35.527 mg/ml and anhydrous ethanol 49.7 vol %.

As a result, although the paclitaxel is among the antineoplastic agents which are most widely used as the injection formulation, it has very low solubility in water or other solvents. Therefore, the solubilizers capable of being used for formulating the paclitaxel into the injection formulation are very limited.

SUMMARY OF THE INVENTION

It is an object of this invention to provide a paclitaxel injection formulation which has improved stability and also less toxicity compared to the presently known paclitaxel injection formulation containing polyethoxylated castor oil as the solubilizer for the paclitaxel.

Extensive efforts have been taken to develop an improved paclitaxel injection formulation having less toxicity, greater stability of dilution, and greater shelf life compared to the presently known formulations. As a result of that, it has been determined that an ethylene oxide addition product of palm olein-derived oleic acid is advantageous in view of the toxicity and also the stability when compared to the ethylene oxide adduct of castor oil, and thus have accomplished this invention.

Starting from the palm olein-derived oleic acid as the lipophilic component instead of castor oil, adjusting the addition ratios of ethylene oxide to sorbitan oleate, it has been determined that polyethoxylated sorbitol oleic polyester having the following chemical structure provides the most suitable injection formulation:

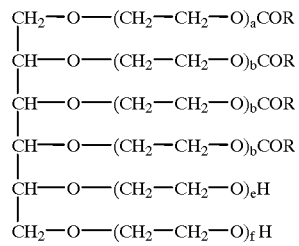

or

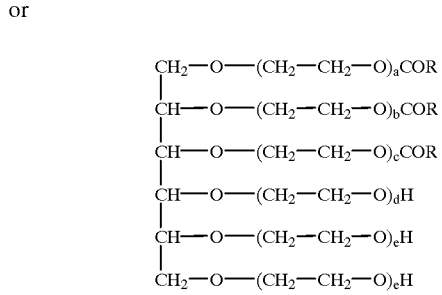

]where a+b+c+d+e+f are the number of the total ethylene oxide addition moles and n is the degree of the carboxylate esterification in moles.

The polyethoxylated sorbitol oleic polyester of the above formula is already well-known in the cosmetic and surfactant industries and are known to have very mild toxicity. See, Kao's Technical Brochure(1998). There are several manufacturers of such a substance in various countries. The polyethoxylated sorbitol oleic polyester is solidified at a temperature below 10° C. This fact restricts partly the use of this substance as the solubilizer for the paclitaxel even if the use of the anhydrous ethanol as co-solubilizer partially prevents the solidification.

Further elaborate trials with polyethylene glycol mono fatty acid ester together with the polyesters result in the formulation showing good applicability at low temperatures and the desirable extended stability upon dilution with saline or dextrose injections. The clear criterion for the suitability of the polyethoxylated oleic polyester as the main solubilizer and polyethylene glycol mono fatty acid ester as the auxiliary solubilizer is in that these solubilizers exhibit good solubility in water and in anhydrous alcohol. Another criterion is in that the combined main and auxiliary solubilizers stay in fluid phase-even at low temperatures.

It is empirically certain that the HLB value of the solubilizers which meet the criteria should be as high as 15 but not less than 13. Actually, we have found that all the tried polyoxyethylene sorbitol polyoleate combined with the polyethylene glycol mono fatty acid ester, which provides the desired formulation, have the HLB value of between 13.5 and 15.

Among the numerous polyethoxylated sorbitol oleic polyesters, it is believed that the poly(ethoxylated)$_{30-60}$ sorbitol poly(oleate)$_{2-4}$ is found to give good results. The auxiliary solubilizer suitable for use in this invention includes, for example, poly(oxyethylene)$_{15-20}$ mono oleate, poly(oxyethylene)$_{15-20}$ mono 12-hydroxy stearate and poly (oxyethylene)$_{15-20}$ mono ricinoleate. Moreover, polyethylene glycol mono fatty acid ester of other fatty acid could be used so long as the HLB value of the mono ester lies in the 13.5 to 15.0.

The polyoxyethylene sorbitol oleic polyester can be produced by the method well known in the art or obtained from various suppliers, for example, Kao Corp., Japan. Most of the polyethylene glycol mono fatty acid esters are produced by the methods well known in the art or obtained from various suppliers, for example, Sanyo Surfactant Co., Japan. When the adjustment work of the ethylene oxide addition is necessary, it can be done in accordance with the methods known in the art.

In the actual experimental formulations, two other components, such as polyethylene glycol and polyvinyl pyrrolidone, to the combined solubilizer, to achieve the quick dispersion of the paclitaxel and also to achieve the extended stability of the formulation up to 5 days. As for maintaining the dilution stability up to 30 hours, the two additional components are not necessary.

DETAILED DESCRIPTION OF PREFERRED EMBODIMENTS

The present invention is an improved formulation containing paclitaxel. This formulation has greater stability and maintains solubility for an extended period of time in solution. Further, the, stable formulation showed less toxicity in animal toxicological studies. This is partially due to good compatibility of the oleic acid derivative with animal cells and the low toxic nature of the ester linkages found in the solubilizer.

As described above, paclitaxel is very insoluble in an aqueous medium. Consequently, the commercial injection is formulated as a concentrate at 6 mg/ml in a solvent mixture of 50:50 by volume of Cremophor EL and dehydrated alcohol. For the administration, the formulation is admixed in a 5% dextrose injection or a 0.9% sodium chloride injection to a concentration between 0.3 and 1.2 mg/ml. As discussed in the literature, the stability of the commercial paclitaxel is 1 to 2 days, which is not long enough for the continued parenteral administration.

Consequently, it was necessary to develop a novel formulation of paclitaxel designed to keep the paclitaxel dispersed for a minimum of 3 days either in saline or dextrose injections. The present invention utilizes the polyoxyethylene sorbitol oleic polyester dissolved in the specific polyethylene glycol mono fatty acid ester admixed with additional components, such as polyethylene glycol as a solvent and polyvinyl pyrrolidone as an accepted dispersant for injection use.

Presented in table I are representative paclitaxel formulations of the present invention.

The typical procedure to prepare the formulation is the same as that of the commercial formulation using Cremophor El. First, the polyoxyethylene sorbitol polyoleate is heated and mixed with polyethylene glycol mono fatty acid ester and polyethylene glycol to obtain a solubilizer mixture. Paclitaxel is dissolved in anhydrous ethanol with povidone as a dispersant and added portionwise to the solubilizer mixture and homogenized. After complete dissolution, the whole solution is filtered through a $0.2\mu$ filter and packed in vials under the nitrogen flux. The paclitaxel used is obtained from Bolak Co., Ltd., Korea and is known to be a purification from taxus cuspidate shootings. Its assay revealed a purity of 99.3% by HPLC.

All the solubilizers were incorporated into the formulation as such from the manufacturers, analyzed and checked for the acid and the hydroxyl value to ensure the minimum existence of the residual reactants. Additionally the heavy metallic and the arsenic levels were checked. Both the anhydrous ethanol and polyethylene glycol 300/400 were pharmaceutical grades. Povidone K-12 was from BASF. Other polyvinyl pyrrolidone of a different K-value could be used.

The following examples are for illustration purposes only and in no way limit the scope of this invention.

EXAMPLE 1

Evaluation of the stability of the injection concentrate

Samples of the formulations 1, 2 and 3 listed in Table I were placed in 5 ml vials stopped with a Teflon-coated stopper, and put at room temperature(20° C.) and at a temperature of 37° C. The sample were withdrawn at 1,2,4 and 6 months and analyzed by HPLC. The results were shown in Table 2.

TABLE 2

|       | Formulation 1 | | Formulation 2 | | Formulation 3 | |
| --- | --- | --- | --- | --- | --- | --- |
| Month | Room Temp (20° C.) | 37° C. | Room Temp (20° C.) | 37° C. | Room Temp (20° C.) | 37° C. |
| 0 | 100.8 |        | 100.6 |       | 100.4 |       |
| 1 | 100.52 | 100.2 | 100.6 | 100.7 | 100.2 | 100.5 |
| 2 | 99.85 | 99.7 | 99.7 | 99.6 | 99.5 | 99.8 |
| 4 | 99.26 | 99.5 | 99.5 | 99.3 | 99.2 | 99.4 |
| 6 | 98.82 | 99.2 | 99.1 | 98.6 | 99.1 | 99.0 |

In all the formulations the change of the paclitaxel content was less than 1.5% after 6 months.

TABLE 1

Formulation of the paclitaxel

|  | 1 | 2 | 3 | 4 | 5 | 6 |
| --- | --- | --- | --- | --- | --- | --- |
| Paclitaxel | 30 mg | 30 mg | 30 mg | 30 mg | 30 mg | 30 mg |
| Povidone K-12 | 80 mg | 80 mg | 80 mg | 80 mg | 80 mg | 80 mg |
| Anhydrous ethanol | 1.5 ml | 1.5 ml | 1.5 ml | 1.5 ml | 1.5 ml | 1.5 ml |
| PEG 300/400 | 1.5 ml | 1.5 ml | 1.5 ml | 1.5 ml | 1.5 ml | 1.5 ml |
| Poly(oxyethylene)$_{60}$ sorbitol tetraoleate | 1.0 ml | 1.0 ml | 1.0 ml | 0.5 ml | 0.5 ml | 0.5 ml |
| Poly(oxyethylene)$_{15-20}$ mono oleate | 1.0 ml | — | — | 1.5 ml | — | — |
| Poly(oxyethylene)$_{15-20}$ mono 12-hydroxy stearate | — | 1.0 ml | — | — | 1.5 ml | — |
| Poly(oxyethylene)$_{15-20}$ mono ricinolate | — | — | 1.0 ml | — | — | 1.5 ml |

*Other combinations of poly(oxyethylene)$_{30-60}$ sorbitol(oleate)$_{2-4}$ with the above mentioned polyethylene glycol(peg) fatty acid mono ester were formulated, but omitted in table 1 for the simplicity.

EXAMPLE 2

Evaluation of the stability of the injection concentrate in solution

Stock solutions in accordance with the formulations 1, 2, 3, 4, 5 and 6 were diluted at ratios of 1:10 and 1:50 in 0.9% sodium chloride solution to give the paclitaxel concentrations of 0.6 and 0.12 mg/ml. The solutions were checked at 1, 5, 10, 24, 48, and 72 hours for the sign of precipitation and cloudiness. In all the formulations, the solution of 1:10 and 1:50 showed no signs of precipitation before 72 hours. In the formulations 4,5 and 6, the stability of dilution exceeded more than 5 days.

EXAMPLE 3

Toxicology study of the solubilizers

In the embodiments of the invention, various combinations of polyoxyethylene sorbitol polyoleate and polyethylene glycol mono fatty acid ester could be used. Also, the mixing ratios of the main and auxiliary solubilizers could be varied.

To get typical toxicological data of the solubilizer combinations, the 50:50% mixture of the poly(oxyethylene) 60 sorbitol tetraoleate with poly(oxyethylene) 15 to 20 monooleate was chosen for the intravenous injection of the solubilizer. The results were reported in Final Report on Stability and Toxicology Study for a New Micellar Solubilizer for Injectable Anticancer Agent, May 1999, Research Institute of Pharmacology, Ewha College of Pharmacy, Cosponsored by Ministry of Health and Welfare Korea and Taxon Biotech. Co. When $LD_{50}$ of the combined solubilizers was compared to that of Cremophor EL, $LD_{50}$ of the former was 3 times higher than that of the latter in the male and female rats.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

We claim:

1. A paclitaxel injection formulation comprising: paclitaxel 30 mg, povidone 80 mg, oxyethylene sorbitol oleate 0.5 to 2.0 ml, (oxyethylene glycol)$_{15-20}$ fatty acid monoester 0.5 to 2.0 ml, polyethylene glycol 1.0 ml, and anhydrous alcohol 2.0 ml, the oxyethylene sorbitol oleate being selected from the group consisting of (oxyethylene)$_{60}$ sorbitol tetraoleate and (oxyethylene)$_5$ sorbitol trioleate.

2. The paclitaxel injection formulation of claim 1, wherein the oxyethylene glycol fatty acid monoester is selected from the group consisting of oleic acid monoester, 12-hydroxy stearic acid monoester and ricinoleic acid monoester.

3. The paclitaxel injection formulation of claim 1, wherein the number of ethylene oxide addition moles of oxyethylene glycol fatty acid monoester is in the range of 15 to 20.

4. The paclitaxel injection formulation of claim 1, wherein the anhydrous alcohol is selected from the group consisting of anhydrous ethanol, anhydrous isopropyl alcohol, anhydrous n-propyl alcohol and t-butyl alcohol.

* * * * *